(12) United States Patent
Orady et al.

(10) Patent No.: US 11,806,581 B2
(45) Date of Patent: Nov. 7, 2023

(54) CONTROL SEQUENCE BASED EXERCISE MACHINE CONTROLLER

(71) Applicant: Tonal Systems, Inc., San Francisco, CA (US)

(72) Inventors: Aly E. Orady, San Francisco, CA (US); Sumner Browning Paine, San Francisco, CA (US); Scott White, San Francisco, CA (US)

(73) Assignee: Tonal Systems, Inc., San Francisco, CA (US)

( * ) Notice: Subject to any disclaimer, the term of this patent is extended or adjusted under 35 U.S.C. 154(b) by 314 days.

(21) Appl. No.: 17/207,038

(22) Filed: Mar. 19, 2021

(65) Prior Publication Data

US 2021/0291021 A1    Sep. 23, 2021

Related U.S. Application Data

(63) Continuation of application No. 16/534,893, filed on Aug. 7, 2019, now Pat. No. 11,000,735.

(Continued)

(51) Int. Cl.
*A63B 24/00*    (2006.01)
*A63B 71/06*    (2006.01)
(Continued)

(52) U.S. Cl.
CPC .... *A63B 24/0087* (2013.01); *A63B 23/03541* (2013.01); *A63B 24/0059* (2013.01);
(Continued)

(58) Field of Classification Search
CPC ............ A63B 24/0087; A63B 24/0059; A63B 24/0062; A63B 71/0622; A63B 23/03541; A63B 2220/808; A63B 2024/0093; A63B 2220/806; A63B 2071/0081; A63B 2220/836; A63B 2230/62; A63B 2071/0655; A63B 2230/062; A63B 2220/833; A63B 2230/436; A63B 2024/0068; A63B 2225/50; A63B 2071/0636; A63B 2071/0627; A63B 2071/0072; A63B 2071/065; A63B 2071/068; A63B 2230/40; A63B 2225/72; A63B 2071/0625; A63B 24/0075; A63B 2225/20; A63B 2220/807; A63B 71/0009; A63B 2071/063; A63B 2071/0638; A63B 2071/0666; A63B 2071/0675; A63B 2220/10; A63B 2220/17; A63B 2220/30;
(Continued)

(56) References Cited

U.S. PATENT DOCUMENTS 5,474,083 A * 12/1995 Church ................. A61B 5/486
                                                    600/595
6,013,007 A *  1/2000 Root .................. A63B 69/0028
                                                    482/902

(Continued)

FOREIGN PATENT DOCUMENTS

WO        2013176933        11/2013

*Primary Examiner* — Garrett K Atkinson
(74) *Attorney, Agent, or Firm* — Van Pelt, Yi & James LLP (57) ABSTRACT

A plurality of control sequences is stored. A user state is detected. A next control sequence associated with the user is selected from the plurality of control sequences based at least in part on the user state.

19 Claims, 7 Drawing Sheets

Related U.S. Application Data (60) Provisional application No. 62/716,861, filed on Aug. 9, 2018.

(51) Int. Cl.
*G16H 20/30* (2018.01)
*A63B 23/035* (2006.01)

(52) U.S. Cl.
CPC ...... *A63B 24/0062* (2013.01); *A63B 71/0622* (2013.01); *G16H 20/30* (2018.01); *A63B 2024/0093* (2013.01); *A63B 2220/806* (2013.01); *A63B 2220/808* (2013.01)

(58) Field of Classification Search
CPC ............ A63B 2220/40; A63B 2220/51; A63B 2220/54; A63B 2220/72; A63B 2220/73; A63B 2220/75; A63B 2220/80; A63B 2230/06; A63B 2230/42; A63B 2230/50; A63B 71/0619; A63B 2071/0658; G16H 20/30; G16H 50/20; G16H 40/63
See application file for complete search history.

(56) References Cited

U.S. PATENT DOCUMENTS

| | | | |
|---|---|---|---|
| 6,347,290 B1* | 2/2002 | Bartlett | G06F 1/1626 715/863 |
| 7,628,730 B1* | 12/2009 | Watterson | A63B 71/0622 482/4 |
| 7,789,800 B1* | 9/2010 | Watterson | A63B 22/025 |
| 8,029,415 B2* | 10/2011 | Ashby | A63B 22/0605 482/49 |
| 8,827,870 B2* | 9/2014 | Dyer | A63B 24/0075 482/9 |
| 9,028,368 B2* | 5/2015 | Ashby | A63B 22/0023 482/4 |
| 9,308,417 B2* | 4/2016 | Grundy | A61B 5/11 |
| 9,530,325 B2* | 12/2016 | Hall | G09B 5/065 |
| 10,052,518 B2* | 8/2018 | Lagree | A63B 22/0076 |
| 10,311,462 B2* | 6/2019 | Lindstrom, Jr. | G06F 16/68 |
| 10,398,379 B2* | 9/2019 | Petisce | G16H 40/67 |
| 10,817,965 B2* | 10/2020 | Rock | G16H 40/63 |
| 10,839,954 B2* | 11/2020 | Flavell | G16H 20/30 |
| 2001/0011025 A1* | 8/2001 | Ohki | H04B 1/086 455/344 |
| 2004/0063551 A1* | 4/2004 | Lightbody | A63B 21/00181 482/8 |
| 2004/0263473 A1* | 12/2004 | Cho | G06F 3/014 345/156 |
| 2006/0189439 A1* | 8/2006 | Baudhuin | A63B 71/0622 482/8 |
| 2008/0051256 A1* | 2/2008 | Ashby | A63B 71/0622 482/1 |
| 2009/0270227 A1* | 10/2009 | Ashby | G16H 20/30 482/8 |
| 2011/0071003 A1* | 3/2011 | Watterson | H04L 67/12 702/160 |
| 2011/0319229 A1* | 12/2011 | Corbalis | G16H 20/30 482/9 |
| 2012/0196256 A1* | 8/2012 | Maeueler | G16H 20/30 434/247 |
| 2012/0220427 A1* | 8/2012 | Ashby | A63B 71/0622 482/4 |
| 2012/0323346 A1* | 12/2012 | Ashby | A63B 24/0003 700/91 |
| 2013/0316316 A1* | 11/2013 | Flavell | G16H 20/30 434/247 |
| 2014/0087341 A1* | 3/2014 | Hall | G09B 19/0092 434/258 |
| 2014/0278125 A1* | 9/2014 | Balakrishnan | G16Z 99/00 702/19 |
| 2014/0298173 A1* | 10/2014 | Rock | G16H 80/00 715/719 |
| 2014/0330186 A1* | 11/2014 | Hyde | A61F 2/70 602/19 |
| 2014/0379273 A1* | 12/2014 | Petisce | G16H 15/00 702/19 |
| 2015/0238817 A1* | 8/2015 | Watterson | A63B 23/0476 482/8 |
| 2016/0271452 A1* | 9/2016 | Lagree | A63B 22/0076 |
| 2016/0346604 A1* | 12/2016 | Lindstrom | A61B 5/1118 |
| 2017/0007882 A1* | 1/2017 | Werner | G01C 21/3676 |
| 2017/0007884 A1* | 1/2017 | Deutsch | A63B 24/0075 |
| 2017/0065873 A1* | 3/2017 | Hall | G09B 5/065 |
| 2017/0172466 A1* | 6/2017 | Eriksson | A61B 5/0022 |
| 2017/0266503 A1* | 9/2017 | Watterson | A63B 71/0622 |
| 2017/0282015 A1* | 10/2017 | Wicks | A63B 24/0075 |
| 2018/0154240 A1* | 6/2018 | Hall | A63B 71/0622 |
| 2019/0282857 A1* | 9/2019 | Hapola | A63B 71/0622 |
| 2020/0047027 A1* | 2/2020 | Ward | G06F 3/0346 |
| 2020/0047030 A1* | 2/2020 | Ward | A63B 24/0087 |
| 2020/0047053 A1* | 2/2020 | Ward | A63F 13/213 |
| 2020/0047054 A1* | 2/2020 | Ward | A63F 13/213 |
| 2020/0047055 A1* | 2/2020 | Ward | A63B 21/0058 |
| 2020/0054929 A1* | 2/2020 | Ward | A63B 24/0021 |
| 2020/0254311 A1* | 8/2020 | Watterson | A63B 22/025 |

* cited by examiner

FIG. 5 actv
 actk
 addr
 crt
 eml
 useridex
 nmf
 gend
 hght
 userid
 lang
 nml
 oth
 pwd
 useridpr
 userimg
 rst
 tz

CONTROL SEQUENCE BASED EXERCISE MACHINE CONTROLLER

CROSS REFERENCE TO OTHER APPLICATIONS

This application is a continuation of U.S. patent application Ser. No. 16/534,893, entitled CONTROL SEQUENCE BASED EXERCISE MACHINE CONTROLLER filed Aug. 7, 2019 which is incorporated herein by reference for all purposes, which claims priority to U.S. Provisional Patent Application No. 62/716,861 entitled VIDEO CENTERED MACHINE CONTROLLER filed Aug. 9, 2018 which is incorporated herein by reference for all purposes.

BACKGROUND OF THE INVENTION

Exercise machines may improve a person's fitness level, by facilitating aerobic exercise, strength training, or both. Examples of aerobic exercises are those which cause significant rises in heart rate and breathing rates and include machines that simulate the movements associated with sports such as running, cycling and rowing. Treadmills, stationary bicycles and rowing machines are generally single purpose machines and are often owned by individuals. Exercise machines, historically maintained as part of professional gyms, are now being purchased and used at an individual's home. Unlike in professional gyms, users who exercise at home usually do not have access to a personal trainer or coaches who can ensure proper and efficient form on a home exercise machine.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Strength training appliances comprise machines that offer resistance and/or load and are used in gymnasia or shared facility exercise rooms. Free weights and systems of pulleys that may be loaded are a common form of load generation used for exercising muscle groups. Systems that use springs or deflecting members may also be used, and because these systems occupy a relatively smaller volume than weight and pulley systems, they may be used in personal spaces such as a home.

Regardless of the loading mechanism, strength training may not normally simulate an activity compared with an aerobic-only machine that mimics a bicycle or road surface. Muscle condition is enhanced by repetitive loading and to reduce the likelihood of injury following a specific program/routine may minimize the risk of mishap.

Repetitions, colloquially "reps", are used to task the muscles to a point where some minor damage is caused so that physiological processes repair the muscle to a higher level of strength than previously; a rep may be exemplified as a series of a defined number of motions such as lift and lower five times. A group of reps is termed a "set", so a set may be, for example, a sequence of reps such as three lots of 'lift and lower five times' actions. A workout is referred to herein as a collection of sets and a single workout may combine many exercises, each one comprising one or more sets. For a particular user, an "exercise program" as referred to herein generally takes place over an extended time and so may be comprised of a number of workouts each of which may be different as required to meet a particular goal. Note that an "exercise program" is a top level description of a goal and should not be confused with a particular software executable program, although it may be associated with a software/firmware program.

Traditionally, there have been attempts to provide exercise program support to a user with supplementary material and demonstrations; video tape and optical discs have been used as a delivery means and 'workout videos' advertised extensively. These programs or courses are generally fixed and operate independently of the user; it is possible to watch a workout video whilst being completely uninvolved in the activity and the content may simply play to the end without any further attention.

Thus, the delivery of informational content in this form is 'open loop'—there is no feedback and no practical way to ensure compliance with a program or even provide a user to be accountable to themselves. A typical traditional result is that a user overdoes the exercise routine, fails to sustain the effort, results are difficult to see, and this discourages a user. That this is the case is evidenced by the anecdotally high proportion of 'bought once and unused' exercise machinery, coupled with a surge in exercise related injuries at or about the peak sales times for equipment. By contrast, effective programs have been executed when a user participates in a scheduled program at a gymnasium or fitness club under the tutelage of a professional instructor or coach.

Unlike strength training programs, aerobic exercise programs that are machine based have benefited from interactive sessions where a user is able to experience shared activity with those of like abilities and this has been relatively successful in cycling exercises where a "group ride" may be relatively well simulated. Competition with another remote or local user may also spark exercise and inspiration with a drive to 'win'. Connectivity of a controller allows machine settings to be altered so that a group may experience the same load conditions as others in the group over a defined route. It is also possible to mirror scenery on a video screen so that a user experiences group cues that result from following a leader.

Delivery of strength training information is instead more personal and usually one does not directly compete with others, forgoing the drive of winning. There is a need for one-on-one interaction with a program that closely follows the actions of a dedicated coach or personal trainer and which has the ability to determine the level at which the user is operating and then to modify the exercise parameters so as to keep the user within safe bounds. There is also a need for a system that allows an alternative exercise to be substituted, responsive to user performance and deficiencies.

Exemplar Exercise Machine. In one embodiment, an exercise machine passes a load or resistance, against which the user exercises, via one or more lines or cables, to a grip or grips that a user displaces in order to exercise. A grip is positioned relative to the user using a load arm and the load path to the user is steered using pulleys at the load arm ends. The load arm is connected to the exercise machine frame using a carriage that moves within a track that is affixed to the main part of the frame, which frame is firmly attached to a rigid structure. This may be by attaching the frame to a wall or other massive structure such as a gantry. The orientation and position of the exercise machine may be alterable and determined by the target exercise set or user needs.

The exercise machine includes a controller, which monitors and measures user performance as well as determines loads to be applied to the user's efforts. The controller is further coupled to a display that allows instructional information to be presented to the user and with which a user interacts. In one embodiment, a display is incorporated into the exercise machine. In one embodiment, a large format surround screen representing a virtual environment is presented to the user; a virtual reality 3D presentation may also be made using a headset. The exercise machine controller also provides audio information that is related to the visual information from a program store or repository that may be coupled to external devices or transducers to provide the user with an acoustic experience that matches the visual experience.

Control instructions and/or control sequences that set the operational parameters of the exercise machine for controlling the load or resistance for the user may also be embedded along with the user information so that the media package includes everything needed for the controller to run the machine. In this way a user may choose an exercise regime and may be provided with cues, visual and audible as appropriate, that allow the actions of a personal trainer to be emulated, including tactic and/or haptic feedback, and/or changes in user load. The controller may emulate the actions of a trainer using an expert system and thus appear to exhibit artificial intelligence. The user may form a relationship with the emulated coach or trainer that builds trust and this relationship may be encouraged by using emotional cues whose effect may be quantified based on performance metrics gleaned from exercise records that track user performance.

The exercise machine controller may also be coupled to environmental control for the exercise area so that exercise parameters may be optimized, adjusting lighting, temperature and humidity as appropriate for example. The exercise machine may be entirely self-contained or may be connected to a data service that allows the exercise machine's exercise program or programs and operational parameters to be changed, recorded, or otherwise accounted for.

In use, the load arm or arms may be positioned to facilitate the exercise intended. In one embodiment, the exercise machine has two or more load arms that may be positioned independently corresponding generally to right and left limbs of the user. The load or resistance applied, against which a user exercises, is determined by the controller and is provided by one or more actuators, such as electric motors, which may be precisely controlled and facilitates a wide range of exercise parameters. In the case where the actuator is an electric motor, one or more permanent magnet brushless motors having a high pole count can provide the torque supplying the load that may be applied and, for those load ranges outside of the easy operation of the motor system, a gearing mechanism may be used. Such a system may be a gearbox, a worm drive, or a pulley system. Sensors measure user action and this information may be processed by the controller and thus used interactively with the exercise parameters. The exercise machine controller also determines and schedules the actions of the virtual trainer who appears to the user.

A desirable consequence of the use of such an exercise machine, which is responsive to the actions of a user, is that personalization is practical and so a relationship may be developed between the user and the machine that encourages a user at least in part by showing progression to the user and/or holding the user accountable to continue with exercise regimes on the exercise machine, and wherein the virtual coach may help determine which exercise programs are more beneficial to the user. With this virtual coaching, a user may avoid poor exercise form, reduce the chance of injury, and be encouraged to maintain an exercise regimen beyond exercising only by themselves.

Because the controller is able to determine the user status at any time during the exercise period, the exercise conditions may be adapted dynamically and the actions of the virtual trainer may be adjusted in close to real time to reflect these changes, which may build user trust in the exercise machine. This leads to close-to-optimal exercise with the attendant results in physical fitness that are rewarding to the user.

Facilitating and providing instruction and information to an exercising user engaged in strength and endurance training is disclosed. In particular, emulating the services provided by a personal trainer or coach including monitoring/recording the performance of a user, remediating problems as they are detected, and providing encouragement to support the user's exercise is disclosed.

There are at least four basic elements that comprise these services. First, the physical exercise machine itself is a machine that provides the resistance to motion against which the user exercises. Unlike purely mechanical exercise machines, this exercise machine is digitally programmable and thus capable of providing any kind of load-to-movement relationship and is able to alter this responsive to user performance measures. Second, user performance is digitally tracked throughout the exercise period and data is accumulated and stored. Under control of the exercise machine controller, this data may be analyzed and compared with other information if available which allows user exercise to be optimized for the best results. Third, workouts, comprising sets and reps, may be assigned intelligently responsive to a particular user. Typically a user's progress is factored into this selection and further applied dynamically to modify a workout to optimize the exercise. Fourth and finally, the user interface comprises a multimedia presentation that incorporates the programming data that defines the base exercise in use. This process is referred herein as "control sequence management" and/or "video management" and may incorporate other and/or alternate information such as audio or other sensory input/output without limitation.

Figure 1:
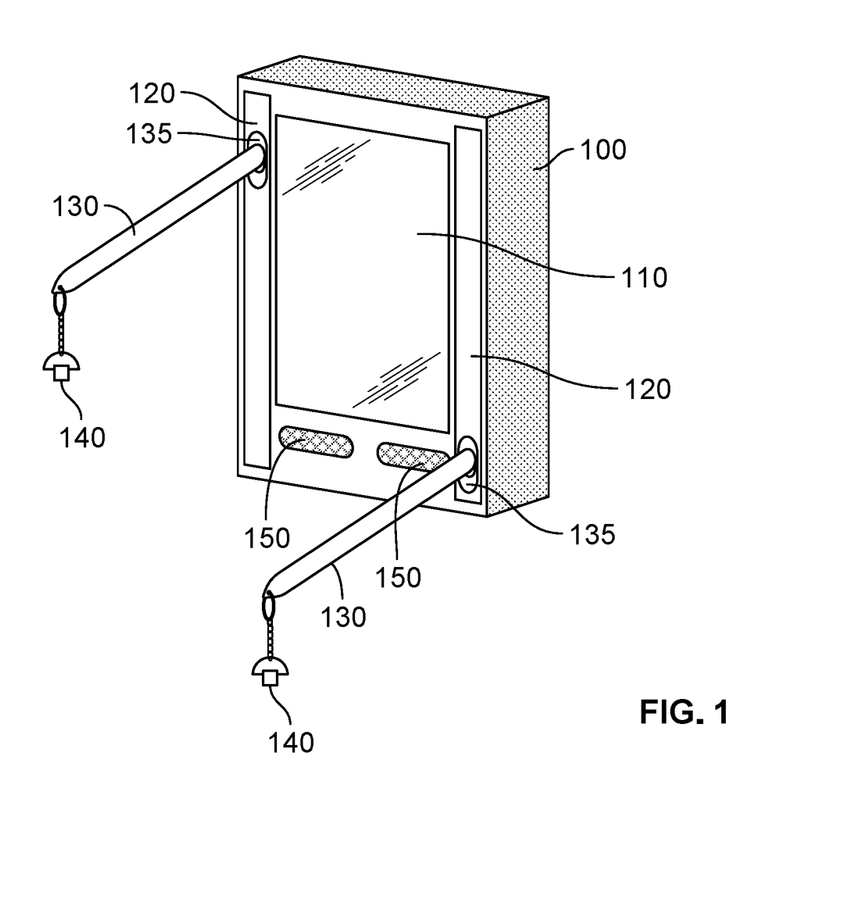
FIG. 1 is an illustration of an embodiment of and exercise machine.

FIG. 1 is an illustration of an embodiment of and exercise machine. Exercise machine frame (100) may be firmly attached to a massive structure so that it may not move during use. Typically this may be a wall and/or other permanent structure, so that the exercise machine is well placed for the user to exercise. It is also possible for a support structure such as a gantry to be used or even a system that allows the exercise machine to be slid away or concealed when the space is required for other purposes; one benefit is that the exercise machine may be used in smaller facilities, such as a small apartment, without impinging upon habitability. In one installation, the exercise machine is located on the underside of a fold up bed that folds into an alcove when not needed for sleeping. When the bed is stowed, the exercise machine is now in its operating orientation.

An integrated display (110) and audio components (150) provide an informational interface for the user, which is driven by the controller, a primary component of the virtual coach services. Two tracks (120), disposed laterally about the display area (110), along which load arms (130) move on carriages (135), are firmly fixed to the exercise machine frame. Examples of a user grip for applying exercise load are shown at (140). These grips and/or stirrups may be used by grasping them with the hands or by inserting a foot to exercise the legs. The connection to the load or resistance element is provided by a cable assembly that is routed by pulleys through the load arm or arms and into the exercise machine.

The display (110) may be any convenient size located for ease of viewing when the user is in the normal position for exercising; typically, exercises may be approximately symmetrical for much of the time with equal loads being provided to both sides of the user, though left and right sides may be exercised simultaneously or sequentially. In one embodiment, asymmetric loads are provided for physically challenged users.

In one embodiment, the display is rectangular having an aspect ratio of 9:16 which provides a pleasing display of an instructor image, whether a person or a representational avatar. The controller may provide video control for many of the standard display formats and in one implementation a number of external ports are provided for driving multiple displays.

External ports may include one or more of a variety of standard or proprietary connections, for example wired or wireless such as WiFi and Bluetooth, that allow external equipment, for example, televisions, mobile phones and tablets, to be attached to the exercise machine. Being able to provide one or more supplementary display units allows the user to participate in exercises where the display panel mounted at the exercise machine is not easily visible, such as when the user faces away from the machine, and this improves the user experience markedly.

The controller provides acoustic information that includes audio information that is synchronized to the visual training information in addition to warning and advisory cues concerned with the operational status of the exercise machine. This audio information may be presented to the user using any of a combination of loudspeakers, headphones or other acoustic transducers. The acoustic path may also include one or more microphones, including ones integrated into wireless headphones or other wireless communication devices, that may pass information to the controller representative of the background and foreground noise in the user's exercise environment. In one implementation the controller detects and monitors the breathing rate of the user. In addition, other physiological sensors may be coupled to the controller.

Figure 2:
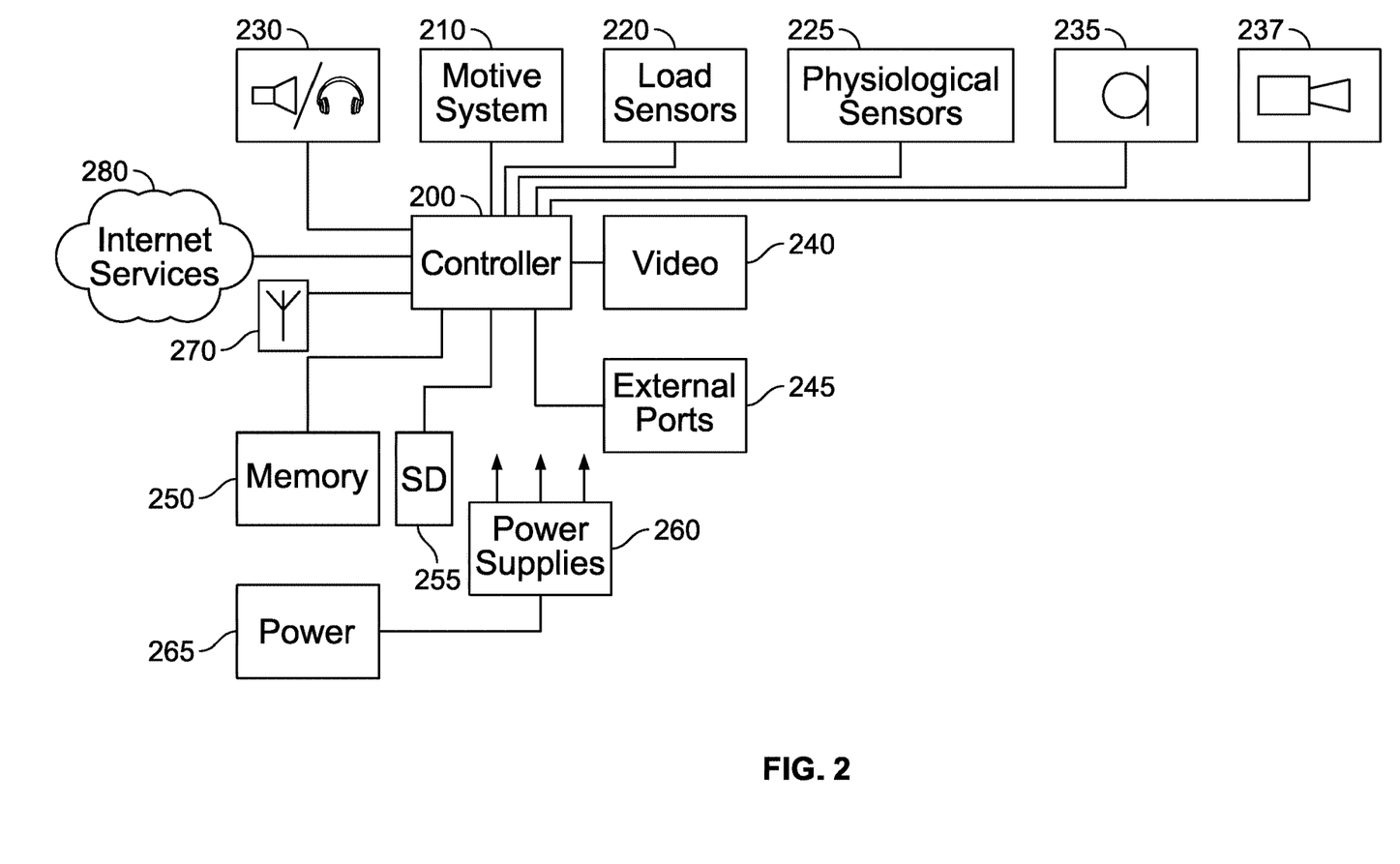
FIG. 2 illustrates an embodiment of the architecture of the exercise machine.

FIG. 2 illustrates an embodiment of the architecture of the exercise machine. In one embodiment, the architecture of FIG. 2 is for the machine of FIG. 1. The exercise machine is comprised of multiple systems and as such requires the use of a controller to coordinate operation of the various parts. For clarity and without limitation the controller (200) is represented as a single device, with any required signal conditioning or power management implemented in the best location for efficiency and performance. Systems like this may alternately be distributed and comprised of elements that are linked so that information may be passed between them as required. For example, sensors that are used for physiological monitoring are often low level devices, so any pre-amplification or signal conditioning may be collocated with the sensor itself. The controller may be implemented in distributed form and, for the elements of the exercise machine that have stored energy, emergency handling systems should, preferably, be local functions to alleviate risk of injury due to failure of critical parts.

Fault detection may be achieved in various ways. Safety considerations require that any unexpected or potentially dangerous operations be detected and remedied. Sudden load application during movement in the course of an exercise may be unpleasant and in some users may cause sprains and strains. It is important, therefore, that some load relief mechanism be provided to limit this risk.

In one implementation, a magnetic clutch is provided that decouples the actuator, such as the motor, from the user-manipulated elements such as the grips/stirrups (140) that are normally used. The controller may detect the unexpected operation by comparing the demanded operation with the actual operation of the actuator. The difference between demand and result may be pre-determined and may invoke a shutdown program that includes depowering the actuator and braking the actuator.

In an electrically actuated exercise machine, one or more current limiting settings may be used to perform this function. In a hydraulic actuator, flow-limiting orifices may be used to perform the function. Snap loads may be limited using magnetic couplings between the actuating cables and the actuator. Load absorption may be performed using spring connections or biases applied to pulley combinations.

The controller may keep a log of all detected error conditions and report these when queried either locally or remotely. Although automatic reset for incidental faults may normally be made available to a user, preferably the user cues the reset in response to information provided by the controller. Hardware limiters may be used to overcome catastrophic failure of the actuator drive and prevent movement until the fault is rectified.

Some elements that are required for safe operation are not shown and are simply assumed to exist, such as a router and firewall function that allows the controller (200) to be linked to a network service (280) such as an internet service (280) and/or a local network (280) without external connection as may be applicable when the exercise machine or a group of exercise machines are operated in a corporate or secure setting, such as a hospital or a gymnasium. In a personal use application, it may not be possible to guarantee that the exercise machine is secure from all forms of attack and so certain parameters may be preset that define limiting conditions for the exercise machine. Detection, containment and recovery from faults may be provided for.

Power is provided for the exercise machine using a power supply (260) that may be connected to power sources (265). Power may be drawn from battery systems or from domestic power line sources. In one embodiment, the exercise machine includes a battery element that provides for a short period of operation following the loss of primary power. This is helpful in guaranteeing that a loss of primary power may be followed by a graceful, controlled shut down.

As referred to herein, "control sequences" include sequences of image, video, audio, and/or multimedia sequences, but also notably sequences that control the exercise machine itself including user load, haptic/tactic feedback, and cadence. The ability of the exercise machine to offer access to an individual or personal trainer which is provided to the user as a control, visual, and/or acoustic set means that this may be defined as a control sequence centered and/or media centered system and the same terminology is used to describe its controller (200). As described above, external ports (245) may support external audio/visual/sensory input/output equipment. The controller comprises one or more processors coupled to interface circuits and includes many of the elements of a typical computer system. The user exercises by working against loads or resistance generated by the machine. In one implementation, these loads are transmitted via cables to the handgrips (140) that are held by the user.

Cable loads are generated by the user working against a motive power system (210) which may be one or more electric motors or other actuator types; for example, hydraulic actuation may be used wherein the pressure and/or flow is controlled, or a screw actuator may be used where the rotation of the screw is powered either electrically or hydraulically. In one embodiment, a permanent magnet brushless electric motor having a high pole count and capable of producing very high torque is used. A particular benefit to using a high pole count motor is that the torque may be held relatively constant as the rotor steps from pole to pole so that there is no sense of pulsing transmitted to the user. Motion and torque or load may be coupled to the cable systems that the user displaces or loads, using a simple drum system that winds the cable in or out, a pulley system that alters the available length of the cable or an equivalent power transmission system.

To monitor the operation of the exercise machine in use, load sensors (220) are connected to the controller. These sensors may include direct or indirect force sensors to measure cable tension that is proportional to the load applied as well as movement sensors that measure displacement of the cables and components. The controller may store this load and displacement data including a time reference as part of its user tracking function. In one embodiment, the cable tension is determined by the force applied to a pulley or pulley assembly that displaces the cable slightly. In another, cable tension is derived from the amount of electrical current being consumed by the motor.

As tension is increased, the cable attempts to straighten, such that force is measured by the strain on this pulley or pulley assembly and this strain is converted to a measure of the tension applied. If the pulley is flexibly mounted, then the displacement of the pulley may be used as a measure of cable tension. The cable movement or displacement may be measured directly, using an encoder coupled to the cable. In one embodiment, the angular displacement of a component to which the cable is tethered is measured and cable displacement calculated or derived. By keeping a record of the cable tension and its displacement, exercise performance and any irregularities may be inferred. In one embodiment, this harvested information is used to modify the exercise parameters to set a performance level and to control irregularities.

Physiological sensors (225) may also provide information to the controller (200). These may include elements such as heart rate, oxygen perfusion information such as SpO2 and respiration rate. These sensors may be worn directly by the user and the data passed wirelessly to the controller. In one embodiment, the sensors are attached by an umbilical wire to a wrist or chest band that the user dons before starting to exercise. In another, a wireless coupling system is used to pass the information and the user wearable apparatus, such as a fitness watch or similar, is provided with a storage location that allows it to be recharged. In yet another embodiment, respiratory information including the expired gas content is passed to the controller. The media controller (200) may detect sensor problems and may offer the user assistance in remedying matters using the display capabilities (240) and (230).

Acoustic information is provided by the controller using audio transducers (230) such as one or more loudspeakers or headphones. The use of wireless links for this function is known and supplementary audio equipment may be added as needed. One or more microphones (235) may be provided that allow the media controller to monitor the user's acoustic environment and this permits the controller to compensate for varying noise levels. In one embodiment, the audio content of a training routine is embedded with an identifying code that enables the controller to detect this identifying information using the microphone and the controller may use this identification data to reduce the risk of unauthorized content affecting the exercise machine or the user. The embedded code may be recovered and decoded by the controller and compared with a white list of permitted content. This content monitoring and its results may be shared with a connected server so that unauthorized or intrusive content may be detected and remedied.

A camera (237) may be used to capture performance information such as posture of the user. Visual content, either stored or streamed live, may be displayed on a display screen (240) that is built into the exercise machine frame. Generally, this content is an important element of the exercise machine. The video information is usually coupled or synchronized with the audio content so that a seamless representation of a human personal trainer or coach may be presented to the user.

Instructional elements may be stored locally in memory (250). This memory may comprise one or more memory types, such as a hard disk drive, a solid-state drive or other non-volatile memory system. A dedicated slot for removable media (255), such as SD Cards, may be provided and this permits easy distribution of exercise data to the exercise machine. Server access may be provided using an internet or similar connection (280) and a wireless link (270) may also be provided for data carriage. In one implementation, a local server provides a central location to which all exercise machines are connected.

Figure 3A:
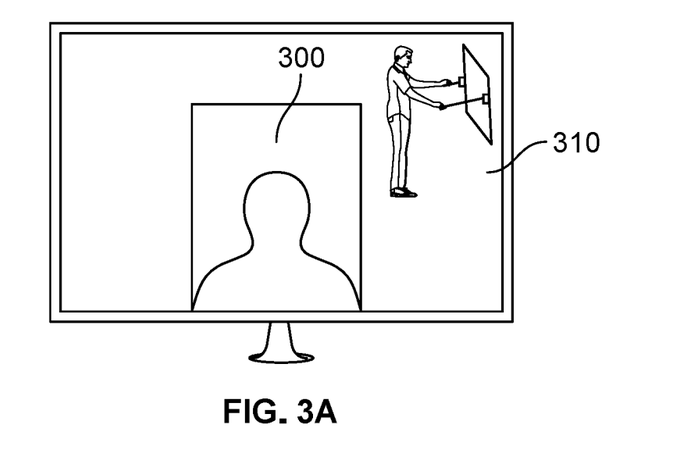
FIG. 3A is an illustration of a first display for an exercise machine display screen.

Example Display Presentation. FIG. 3A is an illustration of a first display for an exercise machine display screen. In one embodiment, the video of FIG. 3A is presented on display screen (240) in FIG. 2. The video presented may be comprised of more than one part; the first part which is the front player or foreground (300), is usually the coach element or the trainer providing the tuition, instruction, feedback or encouragement. The front player is the dominant component for most of the time and may exist independently of anything else displayed on the video display. The second part is a background element (310) that is used to supplement the front player to add cues that are encouraging to the user. For example, a scene representative of others engaged in similar activities provides far more than merely artistic verisimilitude; the human user is generally responsive to a feeling of belonging through joint participation. Accordingly, the background element may be a gymnasium scene with one or more users demonstrating exercises in concert with the coach's descriptive narrative.

Figure 3B:
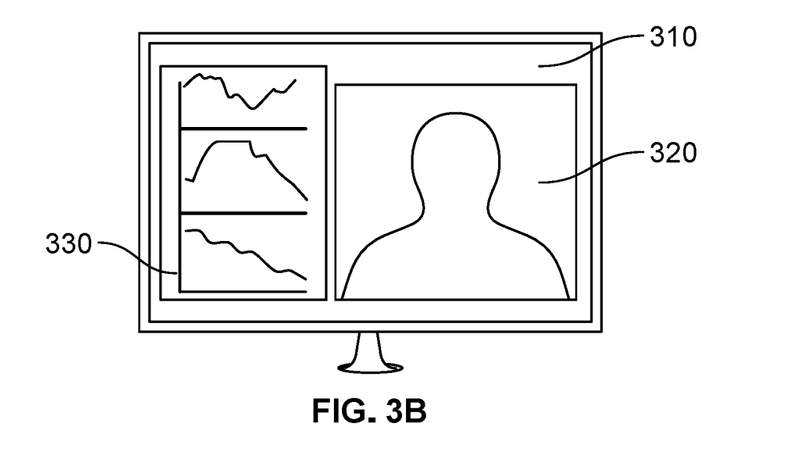
FIG. 3B is an illustration of a second display for an exercise machine display screen.

FIG. 3B is an illustration of a second display for an exercise machine display screen. As shown in FIG. 3B, in addition to the background (310), graphical content (330) may be generated from the user's exercise record as well as an altered foreground or first player (320). This allows the representation of the coach to focus the user's attention on the way that the exercise regimen has evolved over the history of the user and help the user to understand how effective the exercise system has been and what progress has been made.

Figure 3C:
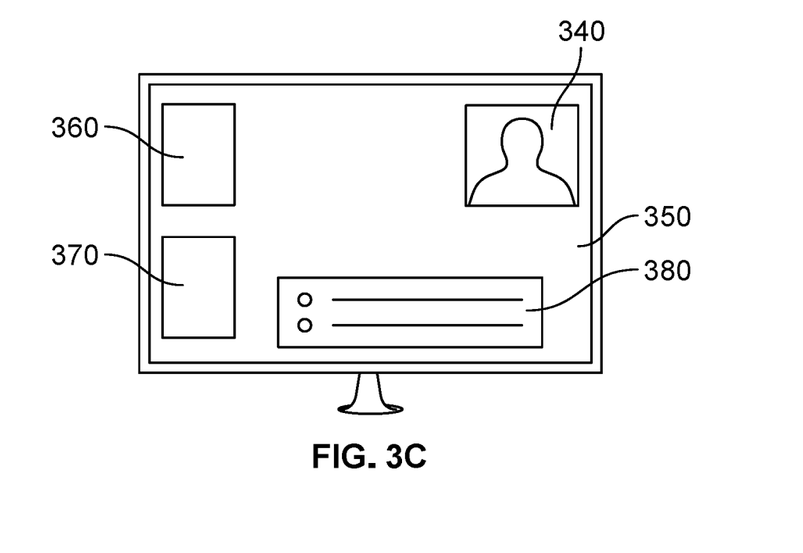
FIG. 3C is an illustration of a third display for an exercise machine display screen.

FIG. 3C is an illustration of a third display for an exercise machine display screen. As shown in FIG. 3C, user data (360) is shown coupled with information as it relates to other users' and/or a normative performance (370). The foreground (340) is shown shrunk to occupy much less of the display area and explanatory information (380) is shown displayed alongside the collected data. The background (310) may be dimmed or replaced (350) with a simpler version to avoid distracting the user during this analysis. This example type of operation is especially valuable when seeking to improve a user's understanding of the objectives of the exercise as well as showing progress explicitly during a coaching session.

User Data. In one embodiment, the exercise machine represents a user within a profile definition. This user profile definition may be stored in any convenient location that is accessible to the exercise machine. Included in this user profile definition is data including the user's personal exercise factors such as body dimensions, shape, weight, age, personal details, and derivatives that allow the effects of exercise to be determined. For example waist size may be used to determine progress against some expectation list. The profile may be a stand-alone record or may be referenced to a statistical model that considers the group of some or all users as a whole or categorically. For example a new user may be recorded as having a waist size that lies at the 80th percentile of users. Other examples of user profile data monitored and/or stored include past performance on the exercise machine and/or other machines/activities, and physiological data from personal activity trackers, mobile phones, wearable sleep monitors, and so on.

Access to the user's profile may be keyed by the user identification. In one embodiment, the user profile draws information from a number of external sources to supplement data that is gathered locally over time from the exercise machine sensors. For example if the user is affiliated with a weight loss group in a social media activity, such as a Fitbit™ activity group, then this information may be incorporated; permitted user information may equally be provided to that group for their own use, subject to user authorization. The user profile workout data provides a historical record of user interactions with the exercise machine, which facilitates the training regimen and the scheduling of exercises.

In this way, multiple users can use any exercise machine client which may then draw user specific information from the server or servers. In another embodiment, the user is identified by a user key which is a SD card that is plugged into the exercise machine at (255) prior to use. In yet another embodiment, chip and pin technologies that incorporate a SIM interface are functionally interchangeable with the SD card memory and may be used as secure user ID and membership credentials, which find use in gymnasium and club settings. In yet another embodiment, the wireless link (270) enables communication with a portable fitness tracker, such as a wrist mounted exercise machine, and uses this information to update a user profile to improve the personalization of the exercise machine. The controller may interact with this information in a similar manner to that used for physiological sensors (225).

A Workout. A user initiates an exercise session by first identifying himself or herself and then entering a sequence of button or touch-screen asserts, responsive to the exercise machine. For example, a user may insert an identification key at (255) to be read by the exercise machine. Information may be entered by a keypad or its equivalent. Physical keypads or virtual keypads may be implemented and in one embodiment a simple handheld remote control is used to enter information, stepping through a selection matrix displayed on the exercise machine screen.

Once a user has selected an exercise program the controller then proceeds to execute a stored program from a collection of stored programs. An exercise program is to be performed over several exercise sessions over a period of time and comprises at least a collection of media components including one or more of audio information and visual information and control information, also referred to herein as the "control program", that produces loads or resistances. The control programs each include fixed information as well as algorithms that calculate control settings for the actuators to enable exercise machine operation for the user.

In general, operation of the exercise machine is comprised of repetitive mechanical operations and, as such, the controller is similar to a state machine, running through a fixed sequence. However, because user performance varies over the course of the exercise period and also between exercise periods, the controller may dynamically modify the control settings that are applied to the actuators to provide the load factors that the user needs over the period of the workout. Structurally, a control program may be stored separately from the media components. The control program may be embedded along with the media data and decoded when that media clip is selected or played. In one embodiment, the embedding is done in the subtitle data of the media clip.

Dynamic Adjustment of Workout. As shown in FIG. 2, the controller (200) evaluates user performance once an exercise has been introduced and the user practices the exercise. The controller may measure the user exercise tempo or cadence through the load sensors (220) and may moderate this by adjusting the load or resistance referred to herein as "dynamic bumping", by changing the actuator operational parameters using the motive system (210) drivers. In one embodiment, the controller (200) is also or alternately responsive to the physiological sensors (225) and monitors heart rate as well as breathing by detecting the sounds detected by a microphone (235).

If the tempo is too slow, the media element being displayed, including the acoustic component, may provide a conscious and/or subconscious hint to increase the tempo. This may be a count, a rhythmic pulse or beat augmented by background video cues or a simple metronome tick provided as background audio via the acoustic transducers (230). Similarly, the same cueing methods may be used to correct a rapid tempo. Changes in the load are applied progressively so that the user does not experience step changes in the load or resistance, as rapid changes may provoke injury. The controller includes a provision for automatic shut down to a safe condition described in a related application.

A Workout Display. During a coached exercise session, the foreground element content (300), with virtual coach video and/or an accompanying audio stream, may be primarily defined by the target exercise. Instruction typically follows a routine that involves a short discussion that describes the exercise itself and the objectives; for example the purpose may be the development of a particular muscle group. During the introduction, the background element (310) is preferably de-cluttered as (350) to reduce or avoid distraction; it is generally preferred that people in the background are de-emphasized since this is known to draw the user's focus away from the coach. Users are students of the coach in this context and an introductory explanation may be a motivation that is an element of successful instruction and encourages that the user's focus be maintained.

Following the introduction, a short demonstration of the exercise enables the user to relate the physical actions to the description. It should be evident that the demonstration may be done by the coach as a foreground activity. However, it is preferred if model users in the background (310) are more prominently displayed whilst the coach assumes a less prominent place on the display screen, such as in a corner position similar to (340). In one embodiment, which exercises have been demonstrated to the user before and which ones have not is tracked, and thus intelligently decides to show them demonstrations only when the user needs to see them, referred to herein as "beginner mode". When the user is already familiar with an exercise, the exercise machine may reduce wasting time with repeated demonstrations, referred to herein as "advanced mode".

Choosing a beginner mode or advanced mode may be referred herein as "static branching". The machine may additionally or alternately operate in different states, without limitation such as novice, intermediate, and expert where the explanations of each exercise are lengthened, shortened or skipped. Thus, if the user is very familiar with the exercises, they might want to just have the trainer lead them through, not demonstrate them. This includes varying the default length of pauses, selecting different segments, or deleting segments.

The video and/or audio tutorial of the program may be pre-determined, but variations may be provided so that this general presentation may be personalized. By way of example, an exercise being delivered for the neophyte user may be accompanied by a discussion that is simple, whereas the same exercise being provided for an advanced user may consider the exercise history of the user and the basic presentation branched as appropriate to fulfill the need for a more sophisticated discussion. As an example of this latter case, alternative phrases may be added or exchanged for simple phrases so 'we'll try to keep working for three repetitions of this exercise' might be exchanged for 'with our improved stamina, this exercise should be easier now and we can aim to do five or six repetitions'. It may be understood that the video element may also be augmented so as to ensure that the user perceives a seamless delivery.

Figure 4:
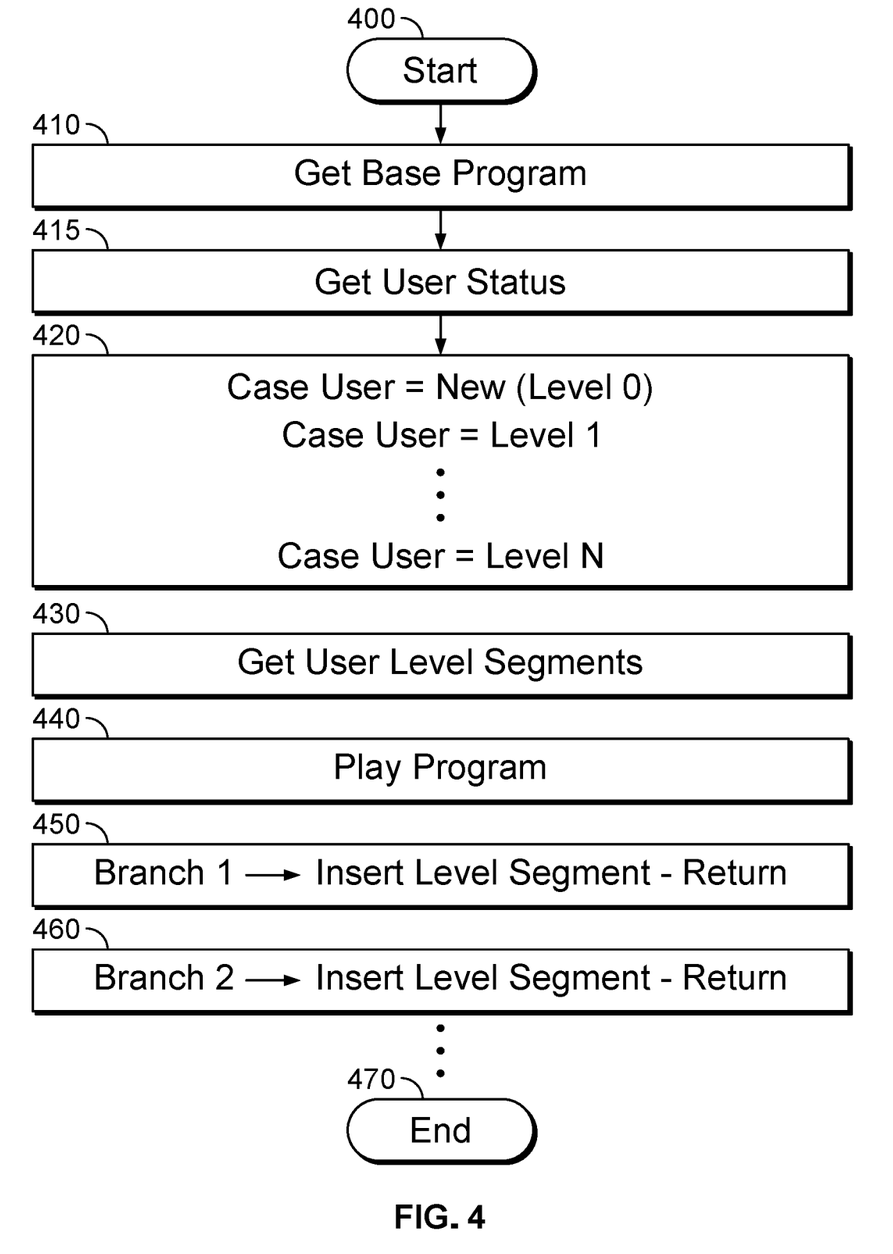
FIG. 4 is a workflow illustrating an embodiment for generating a workout.

Workout Generation. FIG. 4 is a workflow illustrating an embodiment for generating a workout. In one embodiment, the process of FIG. 4 is carried out by controller (200). The program Start (400) causes the initialization of the exercise machine where program constants for the exercise machine are loaded to the proper registers. The selected exercise routine (410) is then accessed from the program repository and the user status (415) is drawn from the user history information that has been collected and stored in non-volatile memory. The user level (420) is a categorical representation of what the user may be expected to be able to do in the context of the selected exercise routine (410). For example, a level 5 user might be expected to perform at a different load and a different cadence/tempo from users at higher or lower levels.

The exercise data (430) appropriate to the user level is retrieved and the routine commenced (440). At the appropriate point (450), where a more advanced exercise element than that provided in the base program (410) is available, then a program branch occurs that replaces the base element with the augmented element that was identified as part of step (430). An augmented element may be a different version of an exercise or the same version of the exercise with more or less explanation depending on the user level. Once the augmented element has concluded, then the program returns to the step following that branch and continues until the next branch (460) where the next basic program element is to be replaced by an augmented element. This process of replacing basic elements with augmented elements continues as a series of branch and return steps until the exercise routine (410) is completed, whereupon the program ends (470).

Dynamic Adjustment of Workout. A program sequence may be assembled in advance of playing the program for the user, but if a user starts to experience difficulty with the exercise sequence then it may be useful to reduce the intensity, referred to herein as "dynamic spotting", as the issue becomes apparent. In this case, a dynamic structuring and restructuring of the program sequence giving emphasis to the user's current performance is preferable. Dynamic spotting is one way to dynamically adjust a workout.

Figure 5:
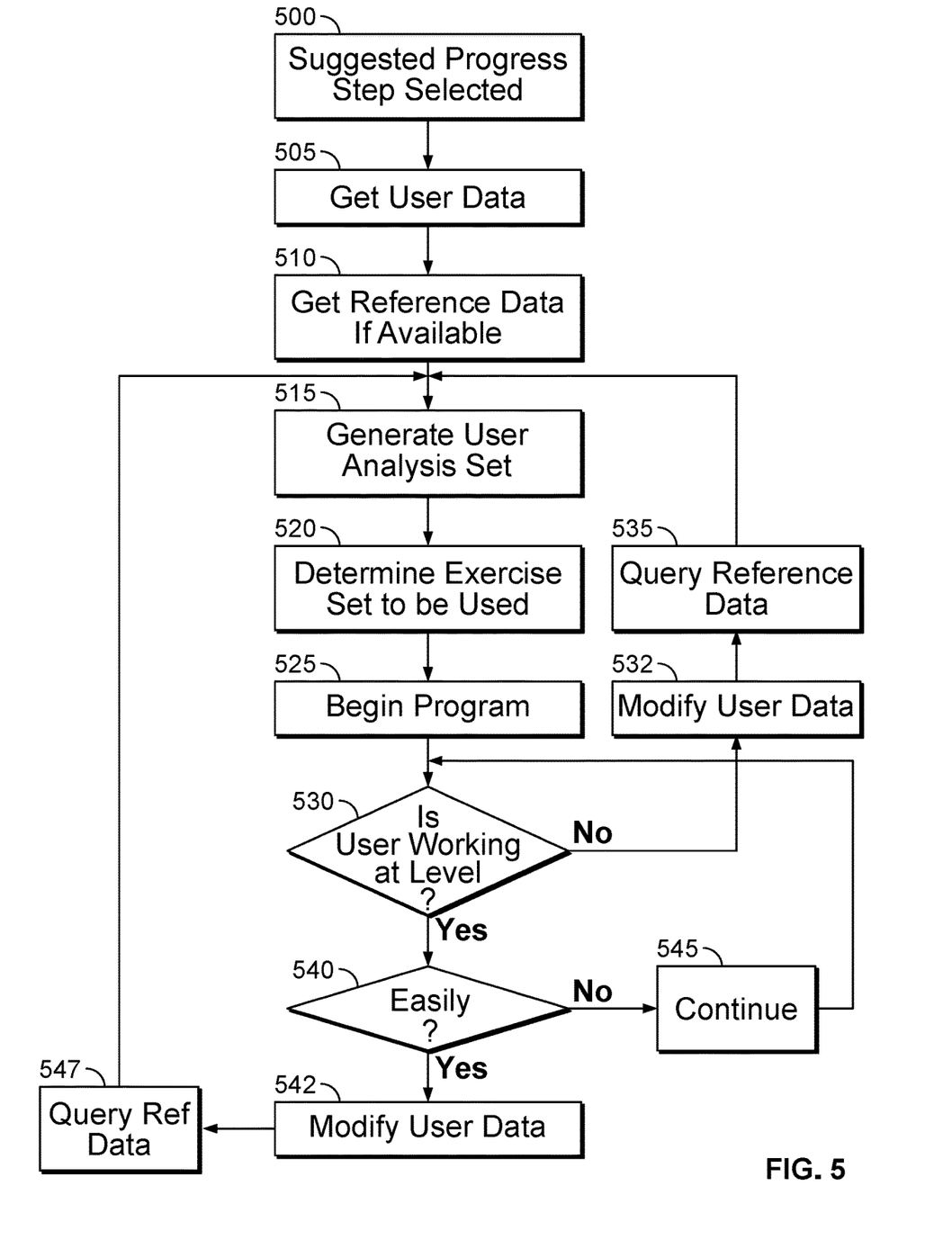
FIG. 5 is a flowchart illustrating an embodiment of a process for dynamic adjustment.

FIG. 5 is a flowchart illustrating an embodiment of a process for dynamic adjustment. For clarity and without limitation, the flowchart describes a loop. For example, if the number of repetitions is achieved, then the set may be deemed completed and the next exercise element might be performed. Sometimes users will not or cannot perform the prescribed number of reps and so they do fewer reps. Other times, the user performs more than the prescribed number of reps, and they do more than was asked in their set. The controller (200) and program adapt to each scenarios, completing the set when the user is actually done, even when that is different than what was prescribed.

If the user performance declines below a predetermined threshold then the exercise might be modified or truncated. As part of the overall fitness goals for a user, the exercise machine maintains a record which provides a planned next step for the user. This may typically be a point on a progress chart or table that suggests a next lesson although it should be clear that a repeat of the last lesson or even an earlier lesson might be appropriate. This determination may be categorical rather than specific since a lesson may be performed at several levels, dependent on the user's proficiency.

In step (500), the suggested exercise set is selected. A useful feature referred to herein as "suggested weights" is a feature where the system has stored, for example, that a user Peter's weight on curls is 34 pounds. Then when Peter does one or more sets, the system may adjust that saved weight setting up or down, depending on how Peter performs the sets.

At step (505), user data is retrieved from storage. This may be local storage (250)/(255) in the exercise machine or may be from a server to which the exercise machine may be connected. The exercise machine may set up a current user parameter data record as available at all times so that the exercise machine is operable independently of remote components. In one embodiment, the user data record may be manually edited by the user so as to create a new record from which an exercise routine may be commenced. A reference data set may be made available so that the range of user performance may be determined and that information retrieved in step (510).

Based on these two data sets, a user analysis may be performed in step (515) so that a suitable exercise program may be selected in step (520). Thus, a program may be chosen for the user based on their profile. This selection may be taken from the set of exercises that meet the progress requirement of the lesson set that was defined in step (500). There are a number of factors that may be used to define the selection, amongst which may be the user ranking in the reference data set and which lessons have been completed, including the rate of progress and the ease with which lessons were completed. Factors that are also relevant may be the amount of load exerted and the number of repetitions completed at that load, coupled with the recovery times between exercise periods. Thus for the suggested weights for Peter in the example above, the system may remember that Peter did 34 pounds on curls the last time. A further factor may be the familiarity of the exercise and fatigue trend information.

Once the exercise set determination in step (520) is processed, and the program retrieved from storage, the user may begin to exercise. Because the exercise machine is able to benefit from the experiences of the entire user population, the range and permutations of likely exercise profiles grows and the process of optimizing any particular program for any particular user becomes increasingly straightforward. The implication is that, for the majority of users, there may be matching experiences already in the record set.

The controller is equipped with sensors and monitors a user's performance. This performance is compared to the predetermined expectations in step (530) and, within a pre-determined tolerance band that may be developed from the population performance information, a decision is made whether or not any modification is needed for the user's program. For example, a user may start off well and over the course of a number of repetitions may exhibit a reduction in the range of motion. The decision may be arrived at that the user is now not working at the expected level and so the user data that was retrieved in step (505) is modified in step (532), the reference data set is queried again in step (535) and an analysis performed again in step (515). If this suggests that the load factors should be altered as a result, then a modification to the program may be performed; it should be noted that this may still be within the set chosen at step (500). The indication of a user performance may be referred to herein as a "quality flag". For the example with Peter above, the system may drop the suggested weight for curls down from 34 pounds together and/or separate from dynamic spotting based at least in part on the quality flag.

If the user is performing as expected, a determination may be made as to the ease of the user's performance in step (540). For example a user that is still operating with the boundaries of a successful workout but is displaying a trend of diminishing output, such as that characterized by tiring, it is likely that the exercise is pitched at the correct level and the operation continues in step (545). However if the user does not exhibit any reduction in performance, such as no increase in timing between repetitions, then it is likely that the user is loafing and not being challenged.

At this point the user data may be modified in step (542) and the reference information queried in step (547) prior to generating a program change at step (515). This program change may be dynamic bumping including a change in the pace or cadence, an increase in load, a change in the load application profile such that more effort is required to achieve the range of motion required or a combination of these factors. For the example with Peter above, the system may increase the suggested weight for curls up from 34 pounds together and/or separate from dynamic bumping based at least in part on the quality flag indicating Peter is not being challenged.

Each modification to the current user-session or workout as a result of generating a new analysis set in step (515) possibly requires a change in the video and the coupled audio segments to properly cue the user to moderate or increase the applied effort. It is preferred if the user cues are provided with sufficient time for the user to respond so that the user does not have to deal with sudden, unexpected changes in the exercise machine operation. This may be done by simply inserting a video snippet or audio overlay informing the user to anticipate a change prior to its invocation, or with another visual/audio/haptic cue.

Escape from this loop may be conditioned upon elapsed time, completion of the required number of repetitions or reaching a performance point which the controller determines to be a working limit for the user at that time. In general the "wind-down" behavior of the exercise machine is tempered to match the inferred state of tiredness of the user so that loads are moderated with a view to reaching approximately zero in the relaxed position.

Celebrating the User. An essential component of a successful exercise strategy is a means for rewarding the user for completion of meeting particular goals. Control programs or sequences may include a celebration routine that provide gratifying events for the user. In one embodiment, the reward is a musical sequence accompanied by a visual sequence displayed to the user. For example, a blue halo around a weight circle may be asserted when the system has determined to dynamically bump a user's load.

In another embodiment, the user earns bonus points which allows the selection of supplementary exercises or graduation to a different competitive level. This latter embodiment may be applied as part of a loyalty program administered by segments of the hospitality industry in which room keys for program participants may comprise the access qualification for a range of perquisites not provided for the general public. One particular benefit of an exercise machine based on a media centered controller is that a fully customized experience is practical and thus may be used to augment certain brands whilst retaining the same basic mechanical design and appearance.

In certain circumstances, a user may be unable to complete an exercise successfully or else may progress to completion at an unexpectedly slower rate. In this case, the controller may provide a diminished or enhanced control sequence. This sequence may be treated as a branch in the program. A program may contain indices which point to branches that may be selected according to a set of exercise metrics which may be pre-determined or calculated. These pointers may be used to indicate the next media component to be executed including repeating the present media component as in a loop instruction.

Figure 6:
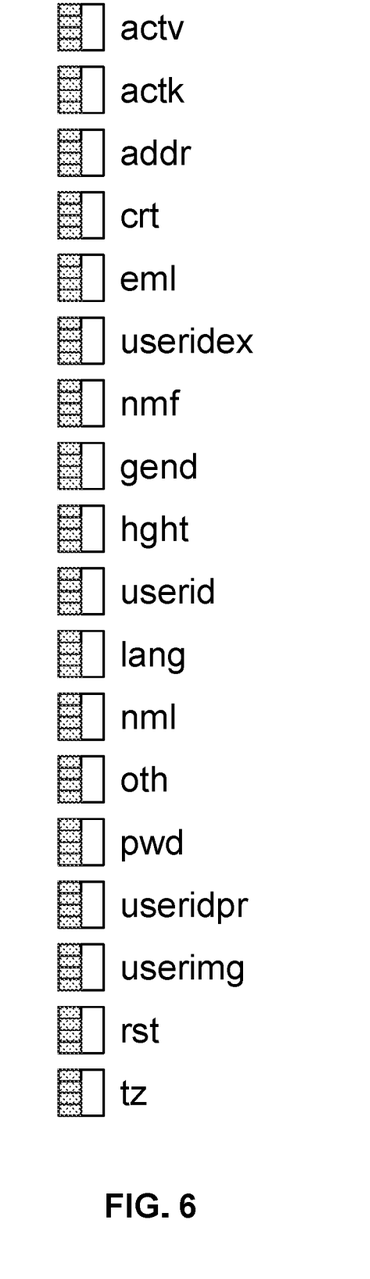
FIG. 6 is an illustration of an embodiment of possible user profile fields.

FIG. 6 is an illustration of an embodiment of possible user profile fields. For example, a user profile may include data on actv—a flag and/or date of an activated license to use the exercise machine and/or user profiling;
actk—a key or identifier of the activated license;
addr—a mailing address for the user;
crt—a date when the user profile was created;
eml—an email address for the user;
useridex—an identifier for an external database, for example a professional gym identifier;
nmf—a first name for the user;
gen—a gender for the user;
hght—a height for the user;
userid—a user profile database index/key;
lang—a language preferred for the user;
nml—a last name for the user;
oth—a miscellaneous key for the user profile;
pwd—an encrypted password for the user;
useridpr—a primary user unique identifier on the server and/or system of exercise machines;
userimg—a content identifier for the user profile image and/or avatar;
rst—a messaging system short code for password resets;
tz—a timezone for a user;
udt—a last modified timestamp for the user profile;
wght—the weight for a user; and
yob—the year of birth for a user.

Live Coaching. In addition to the exercise functions of the exercise machine, the camera (237) and the at least one microphone (235) may also be used as part of a communications link that enables the user to participate directly with a live coach or trainer. Especially where difficulties arise, the exercise machine alone may be unable to make adequate provision for a particular deficiency exhibited by a user. By providing access to a live coach, the problem may be diagnosed and an alternative custom configured control sequence may be provided directly to the user. This sequence may be stored for further use or may be discarded at the conclusion of the consulting session.

Time Flex. Information that is presented to the user may be encapsulated in a collection of video clips or snippets. Presentation of the information may be done by creating a sequence that defines an order in which the appropriate snippets may be shown to the user. The sequence may be predefined, but this is not essential since, when a user performs an initial exercise routine, the next snippet to be displayed may be determined based on the user's performance. In one embodiment, a program of exercises is limited by assigning graduated exercise parameters or limits so that a user who is performing well at a medium level of effort, for example, is not presented with exercises categorized as being advanced and vice versa. In this way the user's risk of injury may be limited, and potential for gains enhanced.

When a user shows signs of tiredness or a lack of performance as referenced above, another embodiment reduces the level of exercise by modifying the exercise regime, either by providing a slightly less demanding exercise which may have reduced loads against which the user works. In this case the visual element of the snippet may be the same, but the load parameters may be lessened to accommodate the user's difficulties, for example by dynamic spotting and/or dropping the suggested weight. In one embodiment, time delays are introduced; some users may wish to pause briefly between reps even though the actual reps may be performed at a proper cadence, whereby this might introduce a significant mismatch in the delivery of the coaching video segments.

To address this mismatch in delivery, a "time flex" technique may be employed to displace the start of the video element and then synchronize this with the motion of the machine caused by the user. This capability to allow the user to influence the rate at which coaching occurs mimics the actions of a human coach or trainer.

One method of time flex includes starting video clips for an exercise movement and forming two program loops. In an outer program loop, the next group of video clips is played. In an inner program loop within the outer program loop, for each of the group of video clips being played, it is determined whether the user is done. If no, control remains in the inner loop, and if yes, the inner loop is broken out of if the user moves on to another movement with a corresponding group of clips, or the inner and outer loops are broken out of if the user is done. In this way, the video/control sequences may be flexible and customized in time to a specific user, depending on if they are slower or faster.

Figure 7:
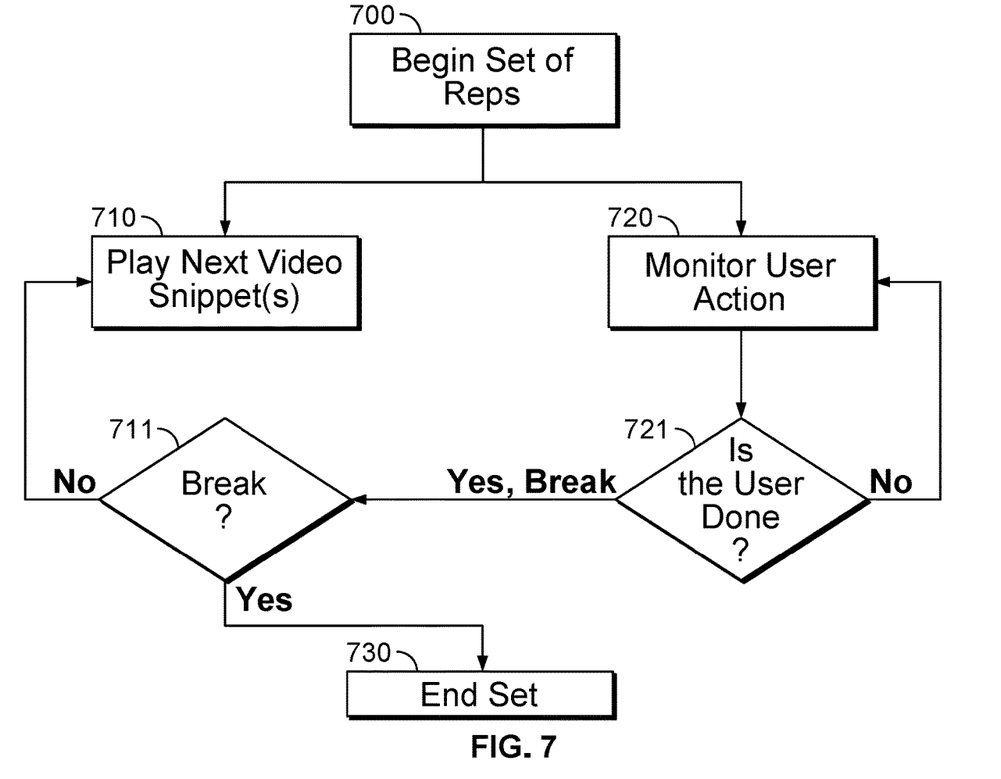
FIG. 7 is a flowchart of an embodiment of a time flex mechanism.

FIG. 7 is a flowchart of an embodiment of a time flex mechanism. In step (700), the user begins a set of reps for an action. In an example described above, an exercise involves a sequence of reps comprising three sets of the 'lift and lower five times' actions. That is lifting and lowering once is one rep, and five of those reps comprise one set.

Steps (710) and (711) address the video being displayed on the display of the exercise machine during the set; and in parallel steps (720) and (721) address monitoring of the user action in performing the set. In a preferred embodiment, these two flows of (710) and (711), and (720) and (721), are asynchronous. That is, they are running at the same time, independently, until in step (721) a break as described below stops the technique. In one embodiment, these steps are synchronous.

In step (710), the control sequence management system (200) plays the next video snippet for this set. Concurrently with step (710), this system in step (711) monitors for receipt of a break from (721) indicating that the user is done with the set. So long as step (711) has received no break instruction, step (710) continues in a loop, continuing to play the video snippets for this set.

In step (720), the exercise machine monitors data generated by the user actions. Examples of such data discussed above include cable tension and cable displacement, as well as data sourced from physiological sensors (225). In step (721), the exercise machine checks if the user is done with the set. As discussed earlier, the user could be "done" before she completes the example five reps of lifting and lowering, or she could be "done" upon completing the five reps, or "done" after completing five or more. Moreover, the user will complete these reps according to the particular and personalized pace and/or cadence of that user during that particular set.

In one embodiment of step (721), the exercise machine determines that the user is done with the set when the cable displacement returns to a cable zero point of one or more of the load arms. At this zero position, the actuator, for example a handgrip, is returned to the end of the arm. In one embodiment of step (721), the exercise machine determines that the user is done when the user instructs the exercise machine to "unrack" the tension, for example by pushing a button or speaking a command. In one embodiment of step (721), the exercise machine determines that the user is done when the user performance declines below a predetermined threshold, and so the set is truncated by the exercise machine rather than by the user Once step (721) has issued the break, the playing of the video snippets for this set in step (720) stops, and the set ends in step (730).

Using the technique of time flex, the video for a set played by the exercise machine matches the duration of the user's performance of that set, no matter how short or how extended that duration is. In this way, the exercise machine mimics the actions of a human coach or trainer.

Insights. The monitoring of user performance trends allows a collection of insights to be recorded as data and action taken on the basis of these insights. For example, if a user displays an increased level of stamina, then the number of times that an exercise element is repeated may be increased. Alternatively, if the user stamina is determined to be significantly greater than was expected, based on the user history, then the load against which the user exercises may be increased by a factor, which factor may be applied using the existing visual snippet as a baseline, for example for dynamic bumping and/or increasing the suggested weight.

To enable this, a video clip or snippet may have associated with it a data string that determines the operational settings for the exercise machine, and which settings may be augmented or diminished according to a factor determined from the performance measurement. Because user records are a useful tool for maximizing the effectiveness of the exercise machine, an exercise period is documented so as to include not only the sequence of the snippets present in a particular exercise session, but also the factors applied to those snippets. For example, if snippet X was used 3 times at a factor of 1.0 followed by it being used at a level 1.15 times greater, then this would be part of the user record. In this way, the next time a user encounters the same snippet it might be useful if the starting point approached 1.1 times the base load instead of the nominal starting value. The above technique may be used to increase the suggested weight.

Video Snippet Tracking. A video snippet may be supplemented by including information that relates to the performance settings for the exercise machine. In one embodiment, the exercise machine settings and commands are embedded with the video information as data using the closed captioning capability or other timeline-synchronized mechanism. In one embodiment, the settings data is pointed to by information stored with the snippet. It is preferred that machine settings are not entirely separated from the data so that the operation of the exercise machine is consistent with the visual information being presented to the user.

If base settings are to be changed, then base settings may still be used as a reference point and a scaling/transformation factor/function applied locally as either predetermined values or else as computed values without disturbing the base data and/or meta-data. Modifying factors may be stored in the user record maintained by the exercise machine so that a particular user may be presented with exercise parameters that continue from the last workout more or less seamlessly.

When modifying factors are used, an informational snippet may be prepended to the exercise snippet to ensure that the user remains informed of the exercise machine settings. In one embodiment, a user may choose to alter the modifying factors within a predetermined range, including the option to reset the exercise machine to its base settings for one or more Reps, Sets or Workouts. For example a user may choose to set the starting value for the set being used to '20% increase'. The user records may be updated to reflect these user selections. If the user habitually chooses to offset the starting value for the exercises and shows no performance deterioration, then for that specific set when used again, the exercise machine may use this habitual setting as a starting point.

In one embodiment, embedded with the video information may be commands to control the user interface. As an example, a command embedded in the video information may invoke the plotting of a chart on screen showing the user the details of their performance for the most recent set. Another command may cause various machine features to be turn on and off, such as a spotter routine or an advanced weight mode such as one emulating chains or an eccentric load.

Summary. An exercise machine responsive to a control sequence and/or media-centered controller (200) that enables a user to interact with a personal trainer or coach without having to be physically present at the same location space and/or same timespace as the coach, that is, the coach may prerecord their coaching. The controller provides exercise machine control synchronized to predetermined lessons or exercise sessions. Exercise sessions may be stored in memory or downloaded from a remote server and sessions comprise one or more media components that give a user a motivational environment within which to exercise. The controller monitors the user's exercising and selects program branches that adjust or modify the base exercise program to optimize the user's performance.

An exercise machine includes a control sequence and/or media-centered controller (200) that provides the user with visual and acoustic cues similar to the interaction a user would experience from a personal trainer or coach. In being responsive to the user's exercise performance, the controller manages the operational parameters of the exercise machine so that the user remains engaged and continues to make progress. The controller may operate autonomously or may operate in concert with a centralized service that allows a user to exercise in isolation, in a shared setting or in a competitive fashion. The controller matches the exercises to the user and provides encouragement as well as alternative exercises to build user ability.

In one embodiment, an exercise machine comprises: a memory; a controller coupled to the memory comprising: a plurality of control sequences associated with a user stored in the memory; a sensor detecting a user state associated with the user; and a processor configured to select a next control sequence from the plurality of control sequences based at least in part on the user state.

In one embodiment, an exercise machine, comprises: a memory storing a plurality of control sequences; a sensor detecting a user state; and a controller coupled to the memory comprising: a processor configured to select a next control sequence associated with the user from the plurality of control sequences based at least in part on the user state.

In one embodiment, the plurality of control sequences is associated with a user workout sequence. In one embodiment, the plurality of control sequences is associated with a user workout video segment. The user workout video segment comprises a advanced mode and/or a beginner mode.

In one embodiment, the plurality of control sequences is embedded within and/or associated with a media clip, and the process of selecting the next control sequence comprises decoding. In one embodiment, the plurality of control sequences is embedded within a subtitle track of a video clip, and wherein selecting the control sequence comprises decoding the subtitle track. In one embodiment, the plurality of control sequences comprises a control sequence associated with a celebration.

In one embodiment, the plurality of control sequences comprises a control sequence associated with a resistance adjustment to a workout. In one embodiment, the plurality of control sequences comprises a control sequence associated with a cadence adjustment to a workout. In one embodiment, the plurality of control sequences comprises a control sequence associated with a conditional branch instruction, wherein the conditional branch instruction is based at least in part on one of the following: the sensor and the user profile.

In one embodiment, the plurality of control sequences comprises a control sequence associated with a loop instruction. In one embodiment, the plurality of control sequences comprises a control sequence associated with a variable assignment. In one embodiment, the plurality of control sequences comprises a control sequence associated with a pointer to a next control sequence.

In one embodiment, the user state comprises a user profile. The user profile may comprise historical information about the user, for example at least one of the following: sleep, activity, food, weight, and stress level, or for example historical information about the user, comprising exercise history, or for example historical information of the user prior to a current workout.

In one embodiment, the user state comprises a current information about the user. In one embodiment, the user state comprises a current information about the user during a current workout. For example, the current information may comprise a number of reps in the current workout, or comprise a quality flag for the user in the current workout, wherein the quality flag comprises a value for a struggling user in the current workout. In one embodiment, the user state may be updated by an external device. For example, the external device may comprise a portable activity tracker.

In one embodiment, the exercise machine comprises an actuator, wherein the actuator is coupled to the sensor. The sensor may comprise at least one of the following: an actuator sensor and a motor sensor. In one embodiment, the sensor comprises at least one of the following: a microphone and a video camera.

Figure 8:
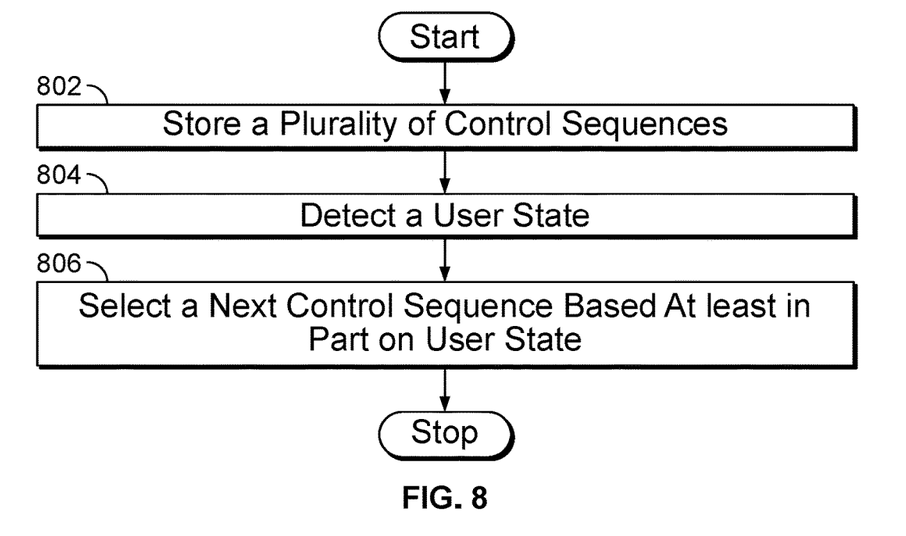
FIG. 8 is a flowchart of an embodiment for controlling an exercise machine.

FIG. 8 is a flowchart of an embodiment for controlling an exercise machine. In one embodiment, the controller (200) of FIG. 2 carries out FIG. 8. In step (802) a plurality of control sequences is stored. In step (804) a user state is detected. In step (806) a next control sequence associated with the user is selected from the plurality of control sequences based at least in part on the user state.

In one embodiment, the next control sequence is associated with a suggested weight. In one embodiment, the next control sequence is associated with an adjustment for time flex. In one embodiment, the next control sequence is associated with a dynamic bumping. In one embodiment, the next control sequence is associated with a dynamic spotting.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. An exercise machine, comprising:
   a frame;
   a first arm located at a left side of the frame and a second arm located at a right side of the frame;
   a user interface located at a front side of the frame;
   a memory storing a plurality of control sequences; and
   a processor, wherein the processor to selects a first control sequence from the plurality of control sequences and controls a manner in which the first control sequence is to be outputted by the user interface, wherein the first control sequence is output by the user interface while at least the first arm, the second arm, or both is being used to perform an exercise, wherein the processor controls the manner in which the first control sequence is outputted by the user interface using time flex.

2. The exercise machine of claim 1, wherein an order in which the plurality of control sequences are output is based on a program of exercises.

3. The exercise machine of claim 1, wherein the processor utilizes time flex to displace a start of a video element and synchronize the video element with a motion of the exercise machine caused by a user.

4. The exercise machine of claim 1, wherein the processor utilizes time flex to repeat a video element until a user has completed an exercise set.

5. The exercise machine of claim 4, wherein the processor determines that the user has completed the exercise set when a cable displacement associated with the first arm and/or second arm returns to a cable zero point.

6. The exercise machine of claim 4, wherein the processor determines that the user has completed the exercise set in response to a button being pushed.

7. The exercise machine of claim 4, wherein the processor determines that the user has completed the exercise set in response to a verbal command.

8. The exercise machine of claim 4, wherein the processor determines that the user has completed the exercise set in response to a determination that a user performance has declined below a predetermined threshold.

9. The exercise machine of claim 4, wherein a next control sequence of the plurality of control sequences is outputted to the user interface in response to the exercise set being completed.

10. The exercise machine of claim 4, wherein a starting point is adjusted based on a number of times the video element is repeated.

11. The exercise machine of claim 1, wherein the first control sequence outputted by the user interface is based on a user level.

12. The exercise machine of claim 11, wherein the user level indicates a load and cadence at which a user is able to perform the exercise.

13. The exercise machine of claim 11, wherein the user level indicates what a user is expected to do in a context of a selected exercise routine.

14. The exercise machine of claim 11, wherein the processor retrieves exercise data appropriate to the user level.

15. The exercise machine of claim 1, wherein user data is modified based on a completion of the exercise.

16. The exercise machine of claim 1, wherein the first control sequence includes a celebration routine.

17. The exercise machine of claim 1, further comprising:
a camera;
at least one microphone; and
a communication link.

18. The exercise machine of claim 17, wherein output from the camera and/or the at least one microphone is provided to a remote user via the communication link.

19. The exercise machine of claim 18, wherein an alternative custom configured control sequence is provided to a user from the remote user via the communication link.

* * * * *